Nov. 7, 1933. F. H. TRAENDLY Plant Pat. 80
YELLOW ROSE
Filed April 20, 1933
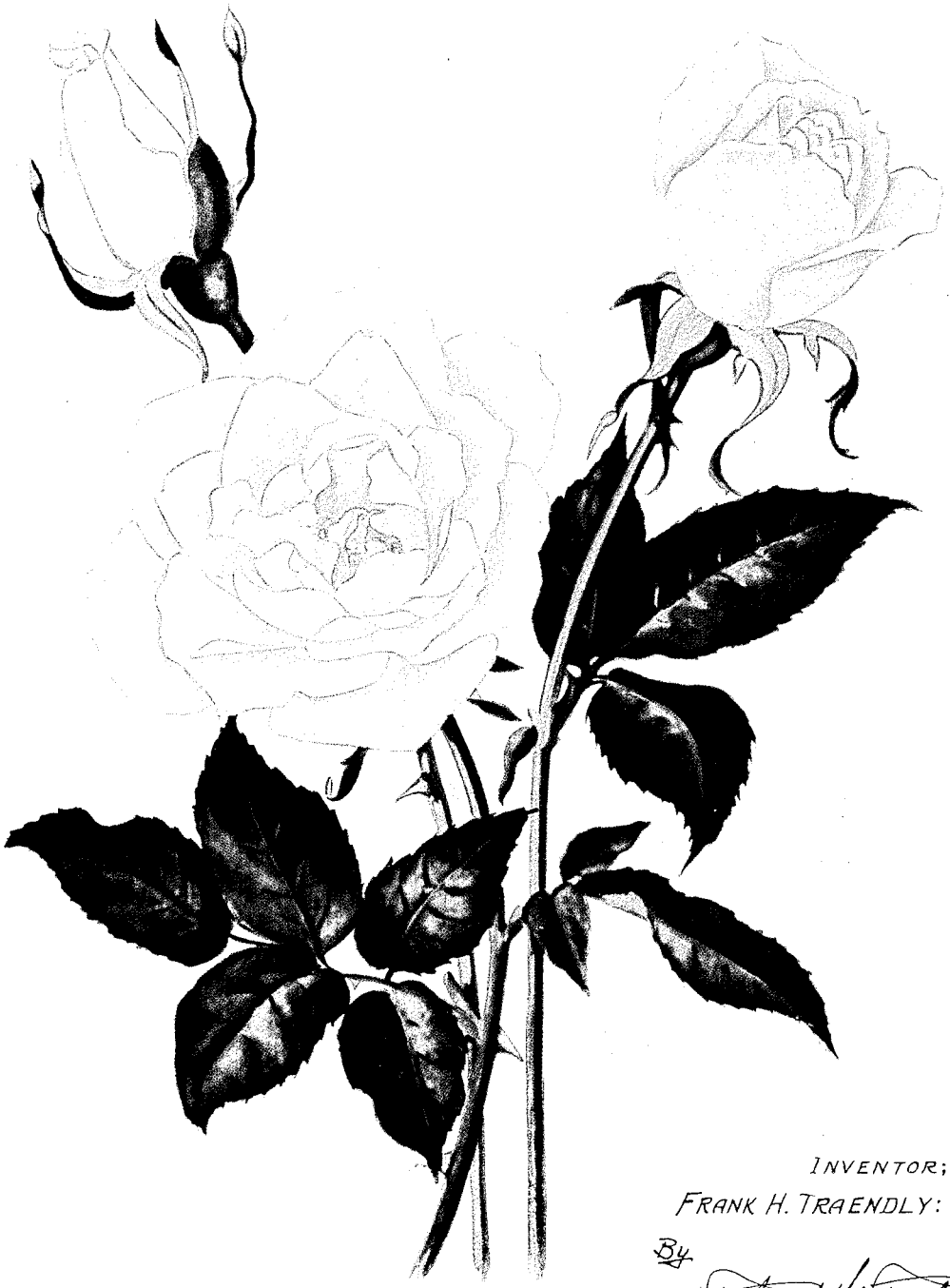
INVENTOR;
FRANK H. TRAENDLY:
By Robert N. Caudle
Attorney Patented Nov. 7, 1933

Plant Pat. 80

UNITED STATES PATENT OFFICE

80

YELLOW ROSE

Frank H. Traendly, Brooklyn, N. Y., assignor to Traendly & Schenck's Rowayton Greenhouses, Inc., Rowayton, Conn., a corporation of Connecticut Application April 20, 1933. Serial No. 667,063

1 Claim. (Cl. 47—61)

This application relates to a new and distinct variety of rose, the same being unique in character, highly delectable in appearance, having a colorature which is especially attractive to one's sight, and which is of superior magnificence throughout.

The accompanying picturization, forming a part of this specification, shows my rose-bloom in three stages of development, that is:—in "embryo", in "evolution", and in "maturity". It must be understood, however, that allowance must be given, in this connection, for differences in soil, the amount of sunshine and shade, or shadow, the humidity of the surrounding atmosphere, and other conditions which will contribute to slight variations in the specific features herein set forth.

My new rose originated as a bud sport of a Talisman rose, at Rowayton Greenhouses, a corporation, at Rowayton, in the State of Connecticut, in January, 1932. It was then asexually propagated by budding, and then by grafting. The perpetuation of its distinctive characteristics has been thoroughly established and fixed, through asexual propagation. My rose required about eight weeks under glass to develop a series of budding eyes, after budding them on healthy and vigorous growing rose plants. This method was practiced in increasing the stock of the variety in question, and if taken on the reasonable assumption that each shoot developed five budding eyes from a single eye, the stock was increased five times every eight weeks, between January 1932 and March 1933. The last series of eyes were cut into scions, instead of being re-budded, and were grafted on Rosa Manetti and these plants were then benched, and are now producing cut flowers in the range of this applicant, in Rowayton, in the State of Connecticut.

Thus far the plants are being grown solely for cut flowers.

My rose has not been tested elsewhere, other than that stated herein, but it is also now being grown in the ranges of the Joseph H. Hill Company and the E. G. Hill Company, both of Richmond, Wayne County, State of Indiana.

My new roses are very large, long pointed and tapering, each extending from its globular symmetrical base, while their upper portions terminate in a flaring, encircling campanulated protuberance, contributing to the beauty of the bud.

The opening of the buds may be delayed three or four days, by placing them in a refrigerator, of from forty to forty-two degrees Fahrenheit, the important point being that they will open naturally when given this treatment without impairing the quality of the bloom.

When first opened the bloom is "globular" and it then expands and flattens out as it opens.

The petals of my rose persist and remain on the stem until the flowers have completely developed and until they wither and shrivel.

The last mentioned feature, manifestly, causes my rose to be particularly adapted to shipment, therefore it is especially adapted to commercial transactions requiring shipment over long distances, or in storage, and for these reasons, coupled with its other delectable features, it is particularly attractive to professional rosarians, and for wholesale and retail purposes in general.

The petalage of the bloom of my rose is double; and it is known as "continuous blooming". Also the firm and full petalage of the bloom thereof gives it a most graceful and pleasing appearance.

The colorature of my rose, taken as a whole, appears as "orange yellow", but when examined analytically the color of the major central portions of the petals is "empire yellow", gradually becoming a picric yellow and shading off to a lighter yellow at the outer edges, with a slight apricot yellow shading at the base portion of each petal. The above is especially true of the inside faces of the petals. These colors are shown in Plate IV, Color Standards and Color Nomenclature, by Robert Ridgway.

The bloom changes color slightly each day, from the empire yellow and apricot yellow described, to a lighter yellow, until it eventually loses the apricot shading, but never losing the rich empire yellow color, even to the point of withering.

The flowers of my rose are self pollinizing.

I have never allowed this variety of rose to produce fruit, as I remove the old flowers before they develop fruit.

The stamens and anthers are large and numerous, and they are orange yellow in color, and the arrangement thereof is regular around the styles. The pollen is lemon yellow in color.

The filaments are medium in size, and are yellow in color.

The stigmas are creamy white in color.

The styles are compact and regular, and are medium heavy.

The ovaries are all enclosed in the calyx.

This plant is a very vigorous growing bush.

The foliage is abundant. The upper side of the new foliage is glossy dark green, and the under side is a dull lighter green. With relation to the old foliage, the upper side is a dull dark green, and the under side is a dull light green.

There are usually five leaflets, sometimes seven, in each compound leaf. The upper side of the new leaves is glossy, the under side is rough. The old leaves are leathery.

The leaves of my new rose are exceedingly long and lanceolated, and are pointed, with relation to their longitudinal axis, but they are comparatively narrow diametrically. Each leaf has a very short exposed portion of its petiole, which continues outwardly throughout the axis of its leaf, with its inner end connected to its leaf-stem, which latter is common to a plurality of leaves. The leaves are also quite attractive in appearance, by reason of the large amount of chlorophyl therein, which imparts to them an unusually dark-green colorature, which is elaborated under the influence of light, thereby causing the bloom, which is associated therewith, to have a more pleasing appearance, especially by reason of the contrast therebetween.

The maximum spread of the bloom, when fully expanded, is from five to five and one-half inches; and the average diameter thereof is four and one-half inches.

The bloom are always borne singly.

The calyx, or receptacle, is not unusual as to color or shape.

The sepals vary, and sometimes show a modified leaf-like form, their color is dark green on the outside and grayish green on the reverse side and they are ceraceous in appearance. In form they are wide at the base, narrowing at the center and spreading at the tip, terminating in a sharp point, they are coarse and irregular serrate. The peduncles grow to a great length, and they are large and straight in form, and are vigorous in growth, and they are provided with only a comparatively few spines, which are distinguished by a red cast in their color. Another important feature of my rose resides in its production and exuding of a highly delectable tea-fragrance, of long duration.

Having now fully shown and described my new rose, what I claim, and desire to secure by Letters Patent of the United States, is—

A new and distinct variety of rose, herein described, characterized by the yellow color of its petals in which the major central portion of each petal is of a comparatively dark yellow, shading off gradually to very light yellow at its outer edge, with a slight yellow shading on its inner portion; the ability of my rose to retain its beauty of colorature and shape to the point of its withering; its vigorous growth as a bush; its continuous blooming quality; its delectable tea-fragrance; and its beauty of shape and appearance.

FRANK H. TRAENDLY.